United States Patent
Pippert et al.

(10) Patent No.: US 6,884,441 B2
(45) Date of Patent: Apr. 26, 2005

(54) PRODUCTION OF DIALYSIS CONCENTRATE FROM A HIGHLY DENSIFIED CONCENTRATE PRESTAGE AND EXAMPLE OF AN APPARATUS FOR USE AT THE PLACE OF DIALYSIS

(75) Inventors: Manfred Pippert, Glasbutten (DE);
Uwe Hildmann, Gehren (DE);
Hans-Gunther Eigendorf, Bad Saarow-Pieskow (DE)

(73) Assignee: Haas Medizintechnik GmbH, Buchholz (DE)

( * ) Notice: Subject to any disclaimer, the term of this patent is extended or adjusted under 35 U.S.C. 154(b) by 103 days.

(21) Appl. No.: 10/231,659

(22) Filed: Aug. 30, 2002

(65) Prior Publication Data

US 2003/0010703 A1 Jan. 16, 2003

Related U.S. Application Data

(63) Continuation of application No. PCT/DE02/00095, filed on Jan. 15, 2002, which is a continuation-in-part of application No. 09/610,016, filed on Jul. 1, 2000, now abandoned.

(30) Foreign Application Priority Data

Jul. 6, 1999 (DE) .......................... 199 31 077

(51) Int. Cl.[7] .......................... A61K 33/14; A61K 33/00
(52) U.S. Cl. .......................... 424/678; 210/647; 424/679; 424/680; 424/681; 424/717
(58) Field of Search .......................... 210/321.71, 646, 210/647; 252/1; 424/678, 679, 680, 681, 717

(56) References Cited

U.S. PATENT DOCUMENTS

| 4,137,168 A | * | 1/1979 | Perrot | .......................... 210/96.2 |
| 4,336,881 A | | 6/1982 | Babb et al. | |
| 5,045,324 A | * | 9/1991 | Mukai | .......................... 424/678 |
| 5,616,248 A | * | 4/1997 | Schal | .......................... 210/647 |
| 5,616,305 A | * | 4/1997 | Mathieu | .......................... 422/261 |

FOREIGN PATENT DOCUMENTS

| DE | 4039471 A1 | 6/1992 |
| DE | 4133652 A1 | 4/1993 |
| DE | 4211455 C1 | 12/1993 |
| EP | 0086553 | 8/1983 |
| EP | 0456928 A1 | 11/1991 |
| EP | 0575970 A2 | 12/1993 |
| EP | 0697220 A1 | 2/1996 |

* cited by examiner

*Primary Examiner*—John Kim
(74) *Attorney, Agent, or Firm*—Greer, Burns & Crain, Ltd.

(57) ABSTRACT

In contrast to the prior art, the essential components of dialyzing liquids are not provided as a dry concentrate or as a genuine solution at the place of dialysis, but as a suspension of undissolved or incompletely dissolved substances, preferably sodium chloride, optionally sodium acetate, in a solution of the remaining components.

Figure 1:
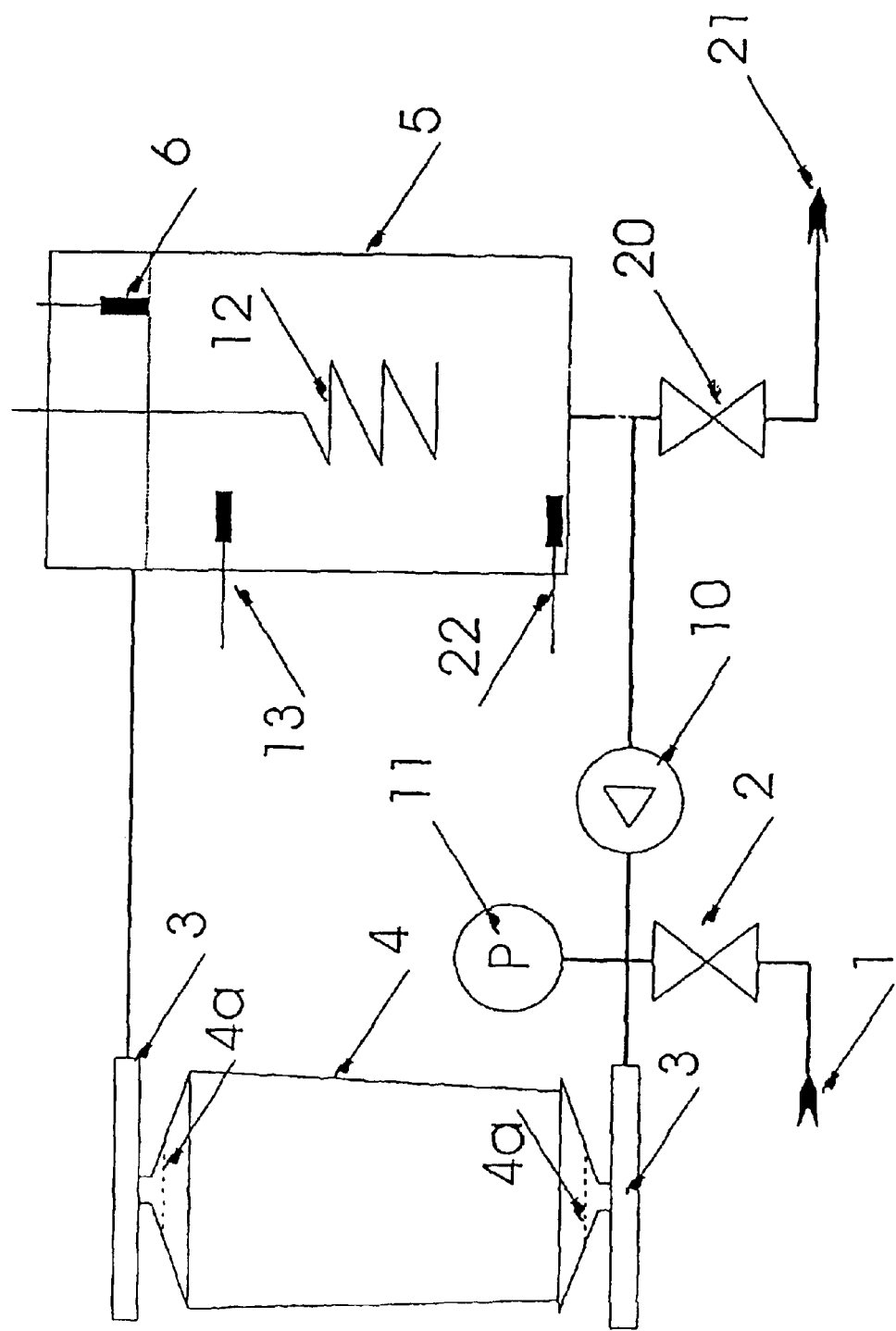

The suspension is prepared, stored, transported and used in a form designated as an acid cartridge or acetate cartridge, respectively.

At the place of dialysis a liquid dialysis concentrate is prepared from the suspension by means of an apparatus, which is here suggested, and can be processed into dialyzing liquid with the existing dosing and safety systems of commercially available dialyzers.

The prestage of a dialysis concentrate, which is described in this invention as a suspension, constitutes the supply form with the highest substance density for the components of acid and acetate-containing dialyzing liquids.

The cost-saving effects and advantages that can be achieved during transportation, storage and handling are achieved without lowering the standards for the patients' safety as are customary in the use of a conventional liquid concentrate.

7 Claims, 1 Drawing Sheet

PRODUCTION OF DIALYSIS CONCENTRATE FROM A HIGHLY DENSIFIED CONCENTRATE PRESTAGE AND EXAMPLE OF AN APPARATUS FOR USE AT THE PLACE OF DIALYSIS

CROSS-REFERENCE

This application is a continuation of co-pending International Application No. PCT/DE02/00095 filed Jan. 15, 2002 which designates the United States of America, and a continuation-in-part of co-pending U.S. application Ser. No. 09/610,016, filed Jul. 1, 2000 now abandoned, which claims international convention priority from German application No. 19931077.7 filed Jul. 6, 1999.

FIELD OF THE INVENTION

The present application relates to methods and apparatus for the supply of components for dialysis treatment, and more particularly for supply of necessary components of dialyzing liquids for use in hemodialysis.

SUMMARY OF THE INVENTION

The present invention relates to a novel supply form for the necessary components of dialyzing liquids for use in hemodialysis, the components being not supplied—in accordance with the prior art—as a liquid concentrate or as a dry concentrate to the dialysis means, but are supplied in the form of a suspension with a higher substance density. Depending on the specification, the raw material content in the suspension is between 72% and 90% of the total mass. Dialysis concentrates which can be mixed in the standard way by dialysis machines to obtain dialyzing liquid are produced from the containers filled with the suspension, e.g. cartridges, with the help of an apparatus as described in this invention at the place of dialysis.

A dialyzing liquid is prepared from the dialysis concentrates prior to performing dialysis on a patient by the dialysis concentrate(s) being mixed with a predetermined amount of water of a suitable quality.

Dialyzing liquid may generally have the following constituents, whose presence or absence and quantitative ratios may vary in response to the respective application: sodium chloride, sodium hydrogen carbonate, glucose, potassium chloride, calcium chloride, magnesium chloride, acetic acid, hydrochloric acid, sodium acetate, calcium gluconate, ascorbic acid, citric acid, hydrates of said compounds, water of a suitable quality for the dialysis and, optionally, further constituents.

In the type of application generally designated as bicarbonate hemodialysis, a so-called "acid concentrate" and a so-called "basic concentrate" are mixed in defined portions with a predetermined amount of water for forming the dialyzing liquid. The basic concentrate always contains sodium hydrogen carbonate or a component to be converted into hydrogen carbonate, optionally further components, excluding alkaline earth salts and acids.

The acid concentrate may contain all of the necessary components, except for sodium hydrogen carbonate.

In the so-called acetate dialysis, use is made of an acetate concentrate which yields a dialyzing liquid solely by mixing with water in defined ratios.

The constituents of the dialysis concentrates are normally dissolved in a production system in defined amounts of water to obtain a genuine solution and are transported as dialysis concentrate to a dialysis station. This requires considerable transportation and storage efforts because of the high amount of water in the solutions.

That is why since some time the basic component preferred for the preparation of the dialyzing liquid, namely sodium hydrogen carbonate, has been supplied more and more often as a powder to the dialyzer and has been dissolved there by adding water to the basic concentrate, with both batch and online methods being employed.

To a small extent it is also customary to provide the components of the acid concentrate for the preparation of the dialyzing liquid in powder form at the place of dialysis, whereby the costs for transportation and storage are reduced. The individual components must then be dosed in situ with high accuracy. This requires considerable efforts with respect to technique and personnel. It cannot be verified in a reliable manner under the given conditions of a dialysis means whether the individual components are actually contained at the predetermined mixing ratio. Moreover, this method is controversial for hygienic reasons. It entails high risks for the patient because an incorrect composition of the dialyzing liquid may be harmful to health and even entail death in an extreme case.

The present invention constitutes a basis for the inexpensive industrial manufacture of a novel prestage of acetate concentrates and acid dialysis concentrates and their use at the place of dialysis for preparing dialysis concentrate. The dialysis concentrate as formed can then be used by the dialysis machine in the standard way for preparing dialyzing liquid.

Said prestage of a dialysis concentrate shows a higher substance density than any other form of supply known from the prior art for supplying the components for hemodialysis, which results in saving effects during transportation, storage and handling without affecting the safety of the dialysis treatment.

According to the invention, all constituents of the acid concentrate are present as a suspension in one container, called "acid cartridge" in the following. This preferred variant, acid cartridge, minimizes the volume of the components of the acid concentrate to be transported, stored and handled to one fifth to one sixth in comparison with conventional acid dialysis concentrates, and the physiologically necessary homogeneity of the concentrate prepared on the dialysis machine can easily be guaranteed by the controlled industrial production, on the one hand, and by the apparatus described hereinbelow, on the other hand.

DETAILED DESCRIPTION OF PREFERRED EMBODIMENTS

Example of an Acid Cartridge

A solution of the following composition is prepared:
  35.58 g magnesium chloride hexahydrate Ph. Eur.
  104.4 g potassium chloride Ph. Eur.
  90.04 g calcium chloride dihydrate Ph. Eur.
  73.62 g acetic acid 100% Ph. Eur.
  385.0 g glucose monohydrate Ph. Eur.
are dissolved in a 1-liter measuring flask with aqua purificata under stirring to 1 liter.

600 ml of this solution and 1264 g sodium chloride Ph. Eur. are dosed into a bottle-like plastic vessel. This yields a pronounced two-phase system in which the liquid-impregnated sediment predominantly contains sodium chloride and the clear supernatant liquid predominantly contains all of the other components of an acid dialysis concentrate. The total volume of said suspension is 1200 to 1210 ml. The raw material content in this example is 83.11%; the water amount is thus 16.89%.

When an acid cartridge of the above content is prepared in the above described way in the apparatus described below, a conventional acid dialysis concentrate (35 times) is obtained for bicarbonate hemodialysis.

This concentrate may be mixed by a dialysis machine in the known way to 210 l dialyzing liquid of the following composition.

| | |
|---|---|
| sodium | 138.00 mmol/l |
| potassium | 4.00 mmol/l |
| calcium | 1.75 mmol/l |
| magnesium | 0.50 mmol/l |
| acetate | 3.50 mmol/l |
| chloride | 115.50 mmol/l |
| bicarbonate | 31.50 mmol/l |
| glucose | 5.55 mmol/l (corresponding to 1 g/l). |

According to the invention, all of the constituents of the acetate concentrate are present as a suspension in one container, called "acetate cartridge" in the following.

When the above-designated cartridges are used, it is possible to maintain the advantages known from the conventional industrial liquid concentrate preparation, as to dosing accuracy, checkability including the legally required traceability, and to achieve, nevertheless, a considerable decrease in volume and weight.

With the invention it is possible to dose the components contained in the dialysis concentrate at a lower weight amount during industrial manufacture at low costs as a solution from a tested larger batch with the necessary and verifiable accuracy into the cartridge body. This guarantees that the dialysis concentrate prepared from the cartridge and the dialyzing liquid subsequently mixed by the dialysis machine have a constant controlled quality and guarantee the patients' safety.

Preferably, the suspension contains sodium chloride as the solid component, and it may here be expedient that other components are also present in a solid form. The solid components are suspended in a solution of the other components. A liquid concentrate, comparable to the standard ready-for-use concentrates, which can be processed with the existing dosage and safety systems of commercially available dialyzers into dialyzing liquid, is prepared from said suspension in the apparatus, which is described further below, on or in the dialysis machine by adding a defined amount of water of a suitable quality in the batch method. The container used for making the acid cartridge or the acetate cartridge may be a dimensionally stable body made from a plastic material or glass, or a flexible bag that is closed in a liquid and gas-tight manner after having been filled with the suspension. It is intended according to the invention that the inlet and outlet of the cartridges are designed such that undissolved components contained in the flowing liquid are retained by a filter when exiting from the cartridge, or the apparatus described below may embody such a filter function.

Furthermore, the invention relates to an apparatus for preparing the cartridges to obtain a concentrate. The apparatus includes a receiving means for the cartridge, which permits a liquid-tight insertion into the circulation system. Furthermore, it includes a batch vessel which is preferably provided with a filling level sensor which after a predetermined filling level has been reached interrupts the further water inflow, as well as lines which connect inlet opening and outlet opening of the cartridge to an inlet opening and outlet opening of the batch vessel, a water inlet and a dialysis concentrate outlet, as well as a pump that makes the supplied water or solution circulate preferably against gravitational force through the batch system until all of the solid components of the suspension have been dissolved and a homogeneous solution is present in the system. This process can be monitored by a control unit by means of sensors or in time-controlled fashion and terminated by a signal for opening the outlet valve.

Said apparatus may be integrated into a dialyzer or may be arranged as a kind of accessory device on the dialyzer, or may be used independently of the place of dialysis for making the concentrate.

Further details of the apparatus for preparing a cartridge will become apparent from the following description of a preferred embodiment and from the attached drawing. The drawing shows such an apparatus in a purely schematic manner.

Water of a suitable quality is fed via a connection 1 into the apparatus. Preferably, the water is derived from the dialyzer and is degassed and has a suitable temperature. In the absence of such water, water of a suitable quality that is otherwise available may be used and can preferably be heated in the apparatus.

After a cartridge 4 has been connected to the two connections 3, an inlet valve 2 is opened so that water preferably enters from below into the cartridge. The two connections 3 are preferably mounted at opposite sides of the cartridge, but can also be positioned side by side at the same side or in any other desired way. The inlet and outlet of the cartridge are each provided with filters 4a preventing undissolved components from exiting from the cartridge. Alternatively, the filter function can be transferred into the batch apparatus. After water has flown into the cartridge, the resulting solution flows into a batch vessel 5. A filling level sensor 6 stops the water supply. The level sensor permits the fixation to different, exactly defined dilution ratios, the entire batch volume corresponding to the sum of the volumes of batch vessel 5, cartridge 4 and the associated flexible tube system.

Alternatively, the volume of the emptied cartridge is not assigned to the batch volume in another version.

The filling level sensor 6 is preferably designed as a conductivity sensor, thereby permitting an additional control of the solution concentration.

After filling of the entire batch volume, a pump 10 is activated which makes the liquid circulate in the system, thereby accelerating the entire dissolution of the solids and effecting homogeneity in time-dependent fashion.

A pressure sensor 11 is provided as a safety monitoring device. Preferably, the apparatus further comprises a heating means 12 for accelerating the dissolution of the solids, as well as a temperature sensor 13. On the one hand, the temperature sensor 13 serves heating control purposes and can, on the other hand, detect the completed state of the dissolution process of the solids in combination with the conductivity-measuring cell 6 with the necessary accuracy.

After the solids have been dissolved completely and the components have been distributed in a homogeneous way, a usable dialysis concentrate is obtained. An outlet valve 20 is now opened to convey the dialysis concentrate through the outlet line 20 to the dialyzer.

The outlet valve 20 may be arranged in front of or behind the pump 10.

Moreover, the apparatus may comprise a level sensor 22 indicative of a minimum liquid level.

What is claimed is:

1. A densified dialysis prestage for the production of a dialysis concentrate to be further converted to a dialyzing liquid for bicarbonate hemodialysis comprising a container, designated as an "acid cartridge", containing water the components essential for preparing dialyzing liquid for bicarbonate hemodialysis, except for sodium hydrogen carbonate, the components being present in said container at a raw material amount of 72% to 90% and water being present in said container at an amount of 28% to 10%, and said dialysis prestage being in and to be used in a non-homogeneous, pronounced two-stage state wherein the components are dissolved in water only in part while large amount remain undissolved.

2. A densified dialysis prestage for the production of a dialysis concentrate to be further converted to a dialyzing liquid for acetate dialysis comprising a container, designated as an "acetate cartridge", containing water and the components essential for preparing dialyzing liquid for acetate dialysis, the components being present in the container at a raw material amount of 72% to 90% and water being present in the container at an amount of 28% to 10%, and said dialysis prestage being in and to be used in a non-homogeneous, pronounced two-stage state wherein the contents are dissolved in water only in part while large amounts remain undissolved.

3. The prestage according to claim 1, wherein there is provided a suspension of at least one powder-like or granular components and of water dissolved components of the prestage.

4. The prestage according to claim 1 wherein there is provided a suspension of a plurality of powder-like or granular components and of water dissolved components of the prestage.

5. The prestage according to claim 2, wherein there is provided a suspension of at least one powder-like or granular component and of water dissolved components of the prestage.

6. The prestage according to claim 2, wherein there is provided a suspension of a plurality of powder-like or granular components and of water dissolved components of the prestage.

7. The prestage according to claim 1, wherein said container is a cartridge that can be inserted into an apparatus for preparing dialysis concentrate.

* * * * *